(12) United States Patent
Twyman

(10) Patent No.: US 7,959,042 B2
(45) Date of Patent: Jun. 14, 2011

(54) IN METERING VALVES FOR PRESSURISED DISPENSING CONTAINERS

(75) Inventor: Paul Twyman, Norfolk (GB)

(73) Assignee: Consort Medical PLC, Hertfordshire (GB)

( * ) Notice: Subject to any disclaimer, the term of this patent is extended or adjusted under 35 U.S.C. 154(b) by 1076 days.

(21) Appl. No.: 11/660,908

(22) PCT Filed: Aug. 26, 2005

(86) PCT No.: PCT/GB2005/003330
§ 371 (c)(1),
(2), (4) Date: Feb. 23, 2007

(87) PCT Pub. No.: WO2006/021797
PCT Pub. Date: Mar. 2, 2006

(65) Prior Publication Data
US 2008/0087688 A1 Apr. 17, 2008

(30) Foreign Application Priority Data
Aug. 26, 2004 (GB) .................................. 0419093.0

(51) Int. Cl.
*B65D 83/00* (2006.01)
(52) U.S. Cl. .................... 222/402.2; 239/338; 137/627.5
(58) Field of Classification Search ............... 222/402.1, 222/402.13, 402.2, 402.22, 402.23, 402.24; 137/627.5; 239/337–338
See application file for complete search history.

(56) References Cited

U.S. PATENT DOCUMENTS 3,019,947 A * 2/1962 Gorman ..................... 222/402.2
(Continued)

FOREIGN PATENT DOCUMENTS
EP     0 801 009    10/1997
(Continued)

OTHER PUBLICATIONS

Search and Examination Report dated May 27, 2005 issued in corresponding Application No. GB0419093.0.
(Continued)

*Primary Examiner* — Kevin P Shaver
*Assistant Examiner* — Andrew Bainbridge
(74) *Attorney, Agent, or Firm* — Smith, Gambrell & Russell LLP

(57) ABSTRACT

A metering valve used with a pressurized dispensing container, the metering valve has a valve stem assembly that slides co-axially within an annular metering chamber that surrounds the valve stem assembly and forms a substantially cylindrical chamber body. The metering valve also has an outer seal at the top of the cylindrical chamber body and an inner seal at the bottom of the cylindrical chamber body. The valve stem assembly has an outlet and an associated passage that is above the line of the outer seal when the metering valve is at rest, and is below the line of the outer seal when the metering valve is actuated, thereby creating a dispensing passage for the metering chamber's contents. The valve stem assembly has an inlet and an associated passage that is above the line of the inner seal when the metering valve is at rest, and is below the line of the inner seal when the metering valve is actuated. This arrangement controls the amount of material and fluid dispensed in each metered dose, as both passages are never open to the metering chamber at the same time. The valve stem assembly forms a straight, central passage extending from an open inner end of the valve stem assembly to a mid-point of the valve stem assembly located longitudinally within the metering chamber. The valve stem assembly has at least two elongated openings in a wall of the valve stem assembly to allow radially-directed flow between an exterior of the valve stem assembly and the central passage, the elongated openings being located to extend either side of the inner seal when the valve stem assembly is in the non-dispensing position. These elongated inlet passages serve to assure that the device is more reliable during use.

33 Claims, 5 Drawing Sheets

U.S. PATENT DOCUMENTS

| | | | | |
|---|---|---|---|---|
| 3,158,179 | A | * 11/1964 | Lehmann | 137/627.5 |
| 3,547,317 | A | * 12/1970 | Green | 222/402.2 |
| 4,702,400 | A | * 10/1987 | Corbett | 222/402.2 |
| 5,632,421 | A | * 5/1997 | Colombo | 222/402.2 |
| 5,938,085 | A | 8/1999 | Conroy et al. | |
| 2004/0129737 | A1 | * 7/2004 | Anderson et al. | 222/402.24 |

FOREIGN PATENT DOCUMENTS

| | | |
|---|---|---|
| GB | 1280229 | 7/1972 |
| GB | 2195986 A1 | 4/1988 |
| GB | 2312418 A | 10/1997 |
| WO | 00/56632 | 9/2000 |
| WO | 02/43794 | 6/2002 |

OTHER PUBLICATIONS

Combined Search and Examination Report dated Jan. 26, 2005 issued in corresponding Application No. GB0419093.0.

* cited by examiner

IN METERING VALVES FOR PRESSURISED DISPENSING CONTAINERS

The invention relates to improvements in metering valves for pressurised dispensing containers.

Pressurised dispensing containers are used for dispensing a wide variety of products from mobile to viscose liquid products, powdered products and the like and typically employ a liquid propellant such as a hydro-carbon or fluoro-carbon having sufficiently high vapour pressure at normal working temperatures to propel the product through the valve. These are commonly used for dispensing pharmaceutical medicaments.

Conventional valves, typically metering valves, for use with pressurised dispensing containers comprise a valve stem co-axially slidable within a chamber body defining an annular metering chamber. "Inner" and "outer" annular seals, which are respectively nearer and further from the bulk storage volume of the pressurised dispensing container, are operative between the valve stem and the chamber body to seal the metering chamber therebetween. The valve stem is generally movable against the action of a spring to a dispensing position, wherein the metering chamber is isolated from the container and vented to atmosphere for the discharge of product.

The valve is usually held in place with respect to the container by a closure which is crimped to the container to thereby form the dispensing apparatus.

Dispensing containers are often used to dispense, amongst other products, powdered or soluble medicaments which are stored in the container, suspended or dissolved in a liquefied propellant. The medicament is dispensed from the container, on actuation of the metering valve, together with the propellant as the propellant boils off. To use a dispensing apparatus comprising a metering valve as described above, a user first shakes the pressurised dispensing container and attached metering valve to agitate the liquefied propellant and medicament. The agitation of the propellant homogenises the suspended or dissolved medicament such that the concentration of medicament in the liquefied propellant is substantially constant throughout the propellant volume in the bulk volume of the dispensing container. The pressurised dispensing container is then inverted such that the valve stem of the metering valve is lowermost and actuated by depressing the valve stem relative to the pressurised dispensing container. The liquefied propellant and medicament contained in the metering chamber is vented to atmosphere where it is, for example, inhaled by the user. On release of the valve stem, the spring restores the valve stem to its unactuated position, whereby the metering chamber can be re-charged with liquefied propellant and medicament from the bulk volume of liquefied propellant stored in the pressurised dispensing container.

The metering chamber of such metering valves may be designed to retain a dose of propellant and medicament by capillary retention or otherwise for a period of time between doses. The metering chambers of such valves tend to be recharged during the return stroke of the valve stem during actuation. It is then necessary to provide adequate sealing means to prevent draining of the propellant and medicament from the metering chamber—a problem known as 'loss of prime'. However, it is difficult to prevent loss of prime, especially for valves which may be actuated only intermittently and infrequently. Loss of prime leads to a sub-standard dose being dispensed which has too little active product within the dispensed aerosol.

To try and avoid the problem of loss of prime, metering valves have been developed which are designed not to retain a dose of product in the metering chamber between actuations when the apparatus is upright, i.e. with the valve stem of the metering valve uppermost. These valves rely instead on the metering chamber being able to fill rapidly and consistently when the apparatus is inverted immediately prior to actuation.

FIGS. 5 and 6 illustrate such a prior art valve. The valve 10' includes an elongated valve stem assembly 11' which protrudes from and is axially slidable within a chamber body 12', the chamber body 12' and valve stem assembly 11' defining therebetween an annular metering chamber 13'. The chamber body 12' is located within a valve body 14' which is positioned within a pressurised container containing a product to be dispensed. The metering valve 10' is held in position with respect to the container by means of a ferrule 15' which is crimped to the top of the container. Sealing between the valve body 14' and container is provided by an annular gasket 16'. The ferrule 15' has an aperture 28' through which an outer section 19' of the valve stem assembly 11' protrudes. A pair of seals 17', 18' of an elastomeric material extend radially between the valve stem assembly 11' and the chamber body 12'. The "outer" seal 17' is radially compressed between the chamber body 12', valve stem assembly 11' and ferrule 15' so as to provide positive sealing contact to prevent leakage of the contents of the metering chamber 13' between the valve stem assembly 11' and the aperture 28'. The compression is achieved by using a seal which provides an interference fit on the valve stem assembly 11' and/or by the crimping of the ferrule 15' onto the pressurised container during assembly. The "inner" seal 18' is located between chamber body 12' and valve body 14' to seal an "inner" end of the metering chamber 13' from the container contents when the valve is in a dispensing position.

The valve stem assembly 11' comprises an upper portion 27' and a stem base 45' which is received on the end of the upper portion 27'. The stem base 45' comprises a cylindrical portion 43' with a central bore 46' in which a part of the upper portion 27' is received as a sliding fit. An inner end of the upper portion 27' of the valve stem assembly 11' is provided with four longitudinally running flutes 60' which extend part way along the length of the upper portion 27' from the distal end of the upper portion 27'. The flutes 60' are separated from one another by ribs 61' and the flutes 60' are shallow enough for the upper portion 27' to comprise a solid core 62'. In the non-dispensing position shown in FIGS. 5 and 6 the flutes 60' provide fluid communication between the bulk storage product contained in the dispensing container to which the metering valve is attached and the metering chamber 13' since the flutes 60' bridge the inner seal 18' as best shown in FIG. 6. Consequently flow into and out of the metering chamber in the non-dispensing position is possible. On actuation, the valve stem assembly 11' is depressed, moving the flutes 60' through the inner seal 18' so as to seal off the dispensing container bulk storage volume from the metering chamber 13'. Further depression moves an outlet port 21' of the valve stem assembly 11' into communication with the metering chamber 13' leading to dispensation of the dose of product contained in the metering chamber 13'.

Compared to capillary retention valves the flow path into and out of the metering chamber 13' has been greatly enlarged. Despite this it has been discovered that with this design of valve it is difficult to ensure that the metering chamber 13' is filled completely and consistently when the valve is inverted. In addition, it has been discovered that the draining of the metering chamber 13', when the apparatus is turned upright, is inconsistent and can leave product within the metering chamber 13' for appreciable periods of time. For these reasons the performance of the valve 10' suffers from drawbacks. Firstly, the initial dose or doses dispensed from the metering valve when inverted can be inconsistent and too divergent from the specified dosage due to poor filling of the metering chamber 13'. Secondly poor drainage from the metering chamber can lead to a non-homogonous dose being taken up by the metering chamber on the next actuation since product may be retained in the chamber from a preceding actuation. This is particular a problem where two actuations of the valve occur close together as is required in may medicament delivery regimes. FIG. 8 is a graph of a test which illustrates the impaired function of the valve. The graph shows shot weight in mg versus shot number for a metering valve 10' of the type shown in FIGS. 5 and 6 and described above with the metering valve being actuated in both upright and inverted orientations. The valve is actuated at a time interval of 10 seconds between actuations and was tested dispensing a inactive product containing 134a HFA propellant with a 10% ethanol co-solvent. Actuation in the inverted orientation represents normal actuation of the valve as would occur when a patient takes a dose. Actuation in the upright orientation allows an assessment of how quickly the metering chamber 13' is draining to be made. As can be seen, the first dose dispensed when the apparatus is inverted can vary significantly from specification (in this case the nominal dispensed dose should be 55 mg). In addition, performance on turning the apparatus upright shows that nearly a full dose may be dispensed, see for example shot numbers 6 and 16. This indicates that the valve is neither filling or draining properly.

It is therefore an object of the present invention to provide a fast filling and fast draining metering valve which alleviates these disadvantages.

Accordingly the present invention provides a metering valve for use with a pressurised dispensing container, the metering valve comprising a valve stem assembly co-axially slidable within an annular metering chamber defined between the valve stem assembly and a substantially cylindrical chamber body, the metering valve further comprising an outer seal extending between the valve stem assembly and the chamber body to seal off an outer duct of the valve stem assembly from the metering chamber when the valve stem assembly is in a non-dispensing position and an inner seal extending between the valve stem assembly and the chamber body, the valve stem assembly comprising a straight, central passage extending from an open inner end of the valve stem assembly to a mid-point of the valve stem assembly located longitudinally within the metering chamber, wherein the valve stem assembly further comprises at least two elongated openings in a wall of the valve stem assembly to allow radially-directed flow between an exterior of the valve stem assembly and the central passage, the elongated openings being located to extend either side of the inner seal when the valve stem assembly is in the non-dispensing position.

Preferably, the at least two elongated openings comprise only two elongated openings in the valve stem assembly. The two elongated openings may be diametrically opposed to one another. The elongated openings may have a width of 0.50 mm to 2.00 mm. Preferably, the elongated openings have a width of 1.00 mm.

The elongated openings may have a length of approximately 4.50 mm. In one embodiment, the elongated openings have a length of 4.20 mm.

The central passage is preferably cylindrical. Preferably, the central passage has a constant internal diameter. Preferably, the central passage has an internal diameter which is substantially equal to a width of the elongated openings. The central passage may have an internal diameter of 0.50 mm to 2.00 mm. Preferably, the central passage has a width of 1.00 mm.

Preferably the elongated openings are orientated longitudinally in the valve stem assembly.

Preferably the elongated openings extend from a mid-point of the central passage to an upper end of the central passage.

The valve stem assembly may comprise at least two parts. The valve stem assembly may comprise a stem part or parts and a cap part.

The cap part is preferably slidingly received on the stem part or parts. The cap part may comprise a plurality of upwardly directed projections which constrain lateral movement of the stem part or parts when the cap part is assembled with the stem part or parts. In addition, the upwardly directed projections may extend upwardly into proximity with an undersurface of the inner seal such that on movement of the valve stem assembly into the non-dispensing position the projections are enabled to contact and displace the inner seal in the event that the inner seal is displaced inwards by the valve stem assembly.

In one embodiment, the cap part comprises a bore and the stem part or parts comprises a tubular extension that is received within the bore when the cap part is assembled with the stem part or parts. Preferably, the stem part or parts define the central passage. Preferably the elongated openings are in the form of slots extending from an upper end of the tubular extension towards the mid-point of the valve stem assembly.

In another embodiment the cap part comprises a bore and the cap part and stem part or parts together define the central passage. Preferably the stem part or parts does not substantially extend within the bore of the cap part. The elongated openings may be in the form of open-ended slots extending from a distal end of the stem part or parts towards the mid-point of the valve stem assembly. The stem part or parts may comprise two dependent legs formed between the open-ended slots.

One or more components of the metering valve may have a layer of one or more polymerised monomers bonded to at least a portion thereof. Preferably the one or more monomers are selected from the group of materials comprising perfluoro-cyclohexane, perfluoro-hexane, tetrafluoroethylene, trifluoroethylene, vinylidene fluoride, vinylfluoride, fluoroethylene, fluoropropylene, a siloxane, a silazane, and a parylene.

Any of the inner seal, outer seal and gaskets of the valve may be formed from any of nitrile, EPDM and other thermoplastic elastomers, butyl or neoprene. Any of the rigid components of the valve, such as the valve body, chamber body and valve stem assembly may be formed from polyester, nylon, acetal, stainless steel, ceramics or glass.

The present invention also provides a metering valve for use with a pressurised dispensing container, the metering valve comprising a valve stem assembly co-axially slidable within an annular metering chamber defined between the valve stem assembly and a substantially cylindrical chamber body, the metering valve further comprising an outer seal extending between the valve stem assembly and the chamber body to seal off an outer duct of the valve stem assembly from the metering chamber when the valve stem assembly is in a non-dispensing position and an inner seal extending between the valve stem assembly and the chamber body, the valve stem assembly comprising a stem part or parts and a cap part, wherein the cap part comprises a plurality of upwardly directed projections, the upwardly directed projections extending upwardly into proximity with an undersurface of the inner seal such that on movement of the valve stem assembly into the non-dispensing position the projections are enabled to contact and displace the inner seal in the event that the inner seal is displaced inwards by the valve stem assembly.

Preferably the upwardly directed projections constrain lateral movement of the stem part or parts when the cap part is assembled with the stem part or parts.

The cap part may be slidingly received on the stem part or parts.

In the following description and claims "inner" and "outer" are used to describe relative positions of components of the metering valve which are respectively further from or nearer to an outer end 19 of valve stem 11 as shown in the Figures.

The valve may be for use in a pharmaceutical dispensing device, such as, for example, a pulmonary, nasal, or sublingual delivery device. A preferred use of the valve is in a pharmaceutical metered dose aerosol inhaler device. The term pharmaceutical as used herein is intended to encompass any pharmaceutical, compound, composition, medicament, agent or product which can be delivered or administered to a human being or animal, for example pharmaceuticals, drugs, biological and medicinal products. Examples include anti-allergics, analgesics, bronchodilators, antihistamines, therapeutic proteins and peptides, antitussives, anginal preparations, antibiotics, anti-inflammatory preparations, hormones, or sulfonamides, such as, for example, a vasoconstrictive amine, an enzyme, an alkaloid, or a steroid, including combinations of two or more thereof. In particular, examples include isoproterenol [alpha-(isopropylaminomethyl) protocatechuyl alcohol], phenylephrine, phenylpropanolamine, glucagon, adrenochrome, trypsin, epinephrine, ephedrine, narcotine, codeine, atropine, heparin, morphine, dihydromorphinone, ergotamine, scopolamine, methapyrilene, cyanocobalamin, terbutaline, rimiterol, salbutamol, flunisolide, colchicine, pirbuterol, beclomethasone, orciprenaline, fentanyl, and diamorphine, streptomycin, penicillin, procaine penicillin, tetracycline, chlorotetracycline and hydroxytetracycline, adrenocorticotropic hormone and adrenocortical hormones, such as cortisone, hydrocortisone, hydrocortisone acetate and prednisolone, insulin, cromolyn sodium, and mometasone, including combinations of two or more thereof.

The pharmaceutical may be used as either the free base or as one or more salts conventional in the art, such as, for example, acetate, benzenesulphonate, benzoate, bircarbonate, bitartrate, bromide, calcium edetate, camsylate, carbonate, chloride, citrate, dihydrochloride, edetate, edisylate, estolate, esylate, fumarate, fluceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylbromide, methylnitrate, methylsulphate, mucate, napsylate, nitrate, pamoate, (embonate), pantothenate, phosphate, diphosphate, polygalacturonate, salicylate, stearate, subacetate, succinate, sulphate, tannate, tartrate, and triethiodide, including combinations of two or more thereof. Cationic salts may also be used, for example the alkali metals, e.g. Na and K, and ammonium salts and salts of amines known in the art to be pharmaceutically acceptable, for example glycine, ethylene diamine, choline, diethanolamine, triethanolamine, octadecylamine, diethylamine, triethylamine, 1-amino-2-propanol-amino-2-(hydroxymethyl)propane-1,3-diol, and 1-(3,4-dihydroxyphenyl)-2isopropylaminoethanol.

The pharmaceutical will typically be one which is suitable for inhalation and may be provided in any suitable form for this purpose, for example as a solution or powder suspension in a solvent or carrier liquid, for example ethanol, or isopropyl alcohol. Typical propellants are HFA134a, HFA227 and dimethyl ether.

The pharmaceutical may, for example, be one which is suitable for the treatment of asthma. Examples include salbutamol, beclomethasone, salmeterol, fluticasone, formoterol, terbutaline, sodium chromoglycate, budesonide and flunisolide, and physiologically acceptable salts (for example salbutamol sulphate, salmeterol xinafoate, fluticasone propionate, beclomethasone dipropionate, and terbutaline sulphate), solvates and esters, including combinations of two or more thereof. Individual isomers such as, for example, R-salbutamol, may also be used. As will be appreciated, the pharmaceutical may comprise of one or more active ingredients, an example of which is flutiform, and may optionally be provided together with a suitable carrier, for example a liquid carrier. One or more surfactants may be included if desired.

The seals and gaskets of the valve may be formed from any suitable material having acceptable performance characteristics. Preferred examples include nitrile, EPDM and other thermoplastic elastomers, butyl and neoprene.

Other rigid components of the valve, such as the valve body, chamber body and valve stem may be formed, for example, from polyester, nylon, acetal or similar. Alternative materials for the rigid components of the valve include stainless steel, ceramics and glass.

Embodiments of the present invention will now be described by way of example only, with reference to the accompanying drawings, in which.

Figure 2:
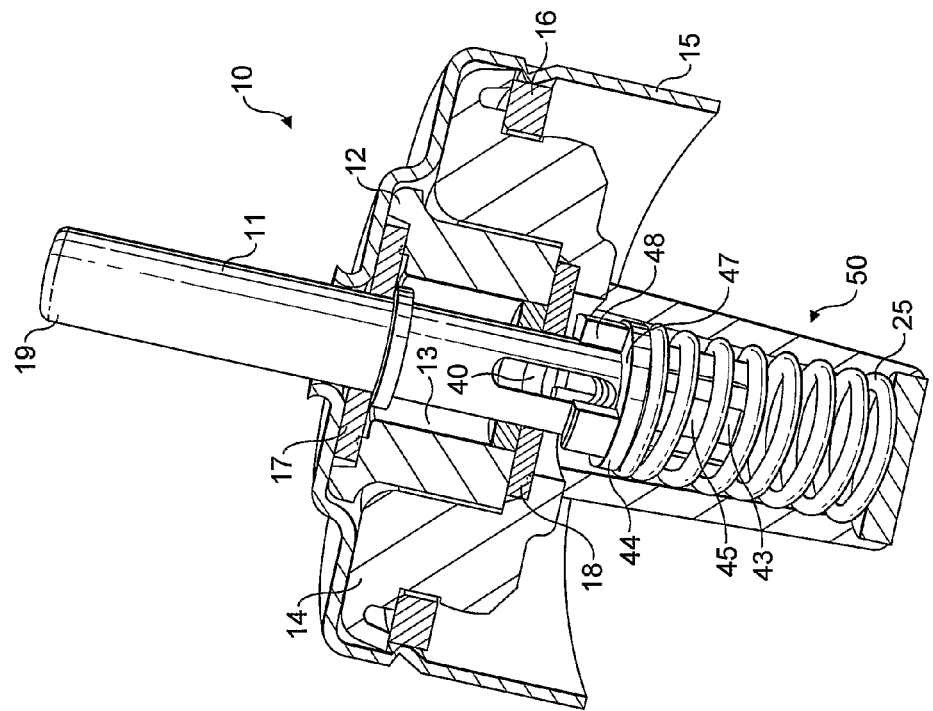
FIG. 2 is a partial cross-sectional view of the metering valve of FIG. 1 with certain internal components shown in perspective view.
Figure 1:
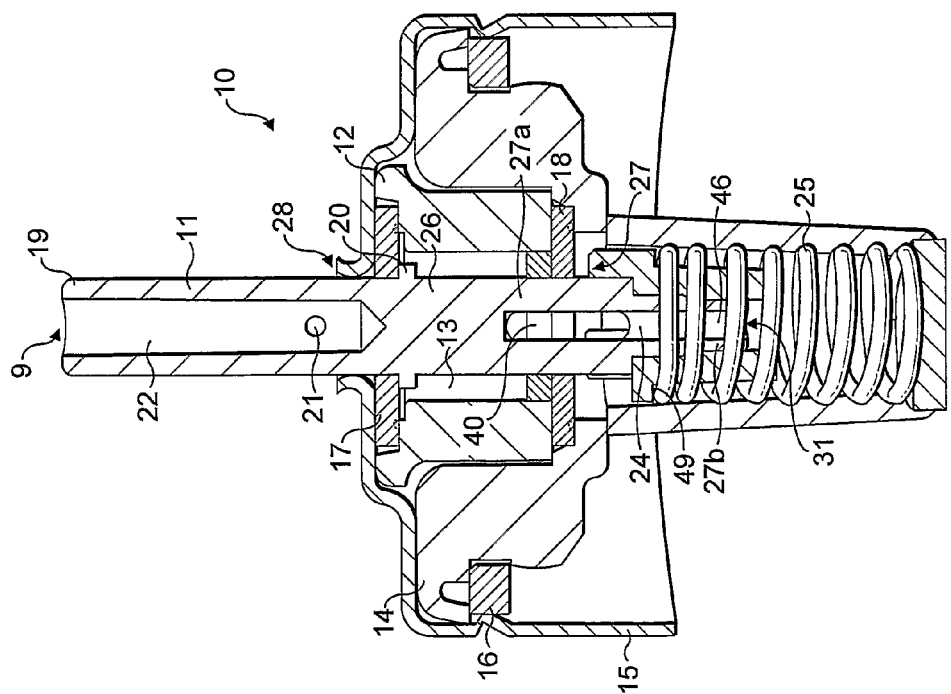
FIG. 1 is a cross-sectional view of a first embodiment of metering valve according to the present invention in a non-dispensing position.

As shown in FIGS. 1 and 2, the first embodiment of valve 10 according to the present invention includes an elongated valve stem assembly 11 which protrudes from and is axially slidable within a chamber body 12, the chamber body 12 and valve stem assembly 11 defining therebetween an annular metering chamber 13. The chamber body 12 is located within a valve body 14 which is positioned within a pressurised container containing a product to be dispensed. The metering valve 10 is held in position with respect to the container by means of a ferrule 15 which is crimped to the top of the container. Sealing between the valve body 14 and container is provided by an annular gasket 16. The ferrule 15 has an aperture 28 through which an outer section 19 of the valve stem assembly 11 protrudes.

A pair of seals 17, 18 of an elastomeric material extend radially between the valve stem assembly 11 and the chamber body 12. The "outer" seal 17 is radially compressed between the chamber body 12, valve stem assembly 11 and ferrule 15 so as to provide positive sealing contact to prevent leakage of the contents of the metering chamber 13 between the valve stem assembly 11 and the aperture 28. The compression is achieved by using a seal which provides an interference fit on the valve stem assembly 11 and/or by the crimping of the ferrule 15 onto the pressurised container during assembly. The "inner" seal 18 is located between chamber body 12 and valve body 14 to seal an "inner" end of the metering chamber 13 from the container contents when the valve is in a dispensing position.

The outer section 19 of the valve stem assembly 11 comprises the discharging end of the valve stem assembly 11 and protrudes from the ferrule 15. The outer section 19 comprises a hollow section 22 with an open upper end 9. The hollow section 22 is closed off within the valve by a solid mid-section 26 of the valve stem assembly 11. The hollow section 22 includes a discharge port 21 extending radially through the side wall of valve stem assembly 11.

A radially-extending flange 20 is provided on the mid-section 26 of the valve stem assembly, located within the confines of the metering chamber 13.

An inner section 27 of the valve stem assembly 11 extends inwardly from the solid mid-section 26 and comprises a hollow section having a central passage 24 in the form of a bore with an open inner end 31 which communicates with an interior of the valve body 14. The inner section 27 has a stepped outer profile. An upper portion 27a of the inner section 27 has an outer diameter equal to the outer diameter of the solid mid-section 26. A lower portion 27b of the inner section 27 has a smaller outer diameter such that the inner section 27 undergoes a step change in diameter between the two portions 27a and 27b.

Two elongated slots 40 are formed in the upper portion 27a of the inner section 27. The slots 40 are orientated along the long axis of the valve stem assembly 11 and extend from the solid mid-section 26 to the step change in diameter of the inner section 27. The slots 40 extend radially through the thickness of the wall of the upper portion 27a allowing fluid communication between the central passage 24 and outside the valve stem assembly 11 via the slots 40. The slots 40 are located diametrically opposite one another as best shown in FIG. 2. The slots have a width of 1.00 mm and a length (along the axis of the valve stem assembly 11) of approximately 4.20 mm. The central passage 24 of the inner section 27 of the valve stem assembly 11 preferably has an internal diameter equal to the width of the slots 40, in the example shown 1.00 mm.

The valve stem assembly further comprises a stem base 45 which is received on the end of the inner section 27. The stem base 45 comprises a cylindrical portion 43 with a central bore 46 in which the inner portion 27b of the inner section 27 is received as a sliding fit. The stem base 45 further comprises a flange 44 having an upper face 47 which, on assembly of the valve, abuts a shoulder 51 formed at the step change in diameter of the inner section 27. Three projections 48 extend upwardly from the upper face 47 into proximity with the undersurface of the inner seal 18 and surround the upper portion 27a of the inner section 27. Preferably, the distal ends of the projections are spaced from the underside of the inner seal 18 by between 0.3 and 0.5 mm when the valve stem 11 is in the non-dispensing position. Openings are located between the three projections 48 such that the top of the stem cap 45 has a castellated appearance. The openings allow unimpeded access for fluid flow into and out of the openings 40. The projections 48 restrain lateral movement of the upper portion 27. In addition, the projections 48 act to realign the inner seal 18 during actuation of the valve 10. During movement of the valve stem assembly 11 into the dispensing position there is a tendency for the inner seal 18 to be dragged inwards, out of the plane of the seal, due to the friction between the seal's inner diameter and the valve stem surface. This is a particular problem early in the life of a valve when the seal 18 is relatively new. Uncorrected, this movement of the seal 18 has the ability over time and many actuations of the valve to create variations in the volume of the metering chamber 13 and hence the dose dispensed. The projections 48 alleviate the problem by contacting and pushing back the inner seal 18 on each movement of the valve stem assembly 11 into the non-dispensing position.

A spring 25 extends between the valve body 14 and an undersurface 49 of the flange 44 of the stem base 45 to bias the valve stem assembly 11 into the non-dispensing position as shown in FIG. 1 in which the flange 20 is held in sealing contact with the outer seal 17.

In this position, the metering chamber 13 is sealed from the atmosphere by the outer seal 17, and can communicate with the bulk storage volume of the pressurised container to which the valve 10 is attached via the slots 40, open end 31 and the central passage 24. Fluid is prevented from by-passing the central passage 24 because of the sealing of the inner seal 18 against the valve stem assembly 11.

Thus, on inversion of the metering valve, so that the outer end 19 of the valve stem assembly 11 is lowermost, the metering chamber 13 will be rapidly charged with liquefied product to be dispensed. It will be noted that the liquefied product can pass from the bulk storage volume of the dispensing container into the valve body 14 via slits 50 formed in the inner part of the valve body 14 as best shown in FIG. 2. On inversion, the metering chamber 13 will initially be filled by gaseous propellant vapour which must be displaced to allow the liquefied product to fill the chamber 13. Liquefied product can flow into the central passage 24 via the slots 40 and the open end 31. The combination of these points of entry for fluid flow has been found to produce excellent displacement of the propellant vapour in the metering chamber 13 and hence excellent filling performance. It is believed that the open end 31 of the central passage 24 creates a jet of fast moving liquid which mixes with and disturbs the liquid-vapour interface in the central passage 24 in the region of the junction between the slots 40 and the inner seal 18. This turbulent action of the jet is believed to decrease the flow restriction at this point leading to better displacement of the propellant vapour.

To actuate the metering valve the valve stem assembly 11 is depressed relative to the valve body 14 such that the valve stem assembly 11 slides axially relative to the chamber body 12. Upon depression of the valve stem assembly 11 the slots 40 slide relative to the inner seal 18 and are closed off by the inner seal 18 thereby isolating the metering chamber 13 from the contents of the valve body 14 and pressurised dispensing container. Upon further movement of the valve stem assembly 11 in the same direction into a dispensing position, the discharge port 21 passes through the outer seal 17 into communication with the metering chamber 13. In this dispensing position, the liquefied product in the metering chamber 13 rapidly boils off and is thus discharged to the atmosphere via the discharge port 21, hollow section 22 and outer end 19.

When the valve stem assembly 11 is released, the biasing of the return spring 25 causes the valve stem assembly 11 to return to its original, non-dispensing position. In normal use the apparatus is often turned upright for storage before the next actuation. The presence of the open end 31 and slots 40 allows for rapid draining of the metering chamber 13.

Figure 5:
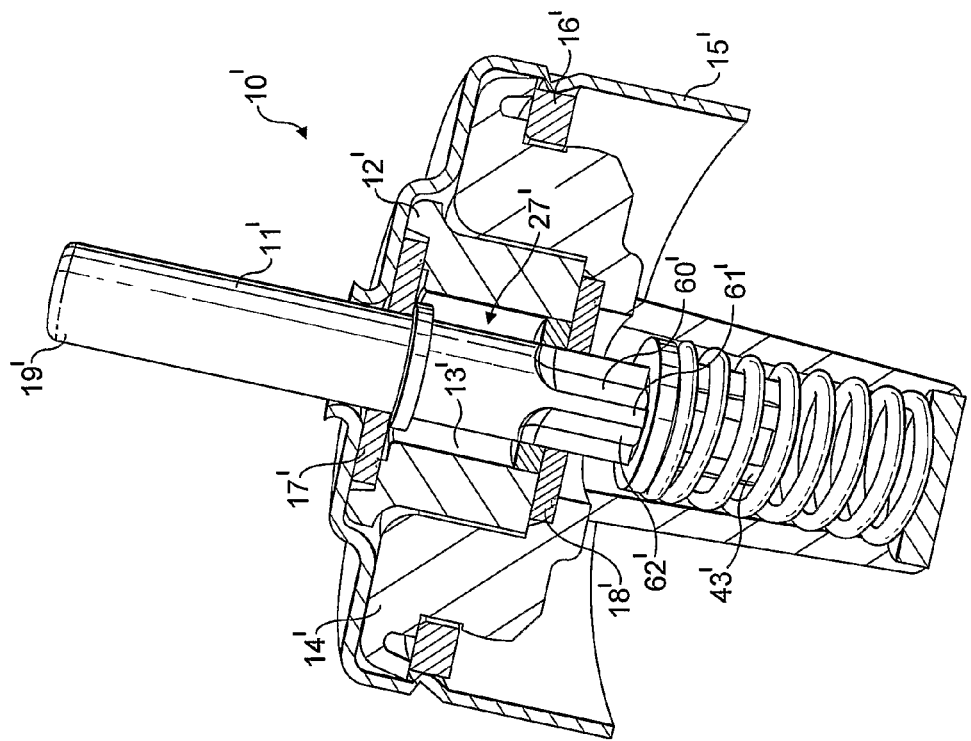
FIG. 5 is cross-sectional view through a prior art metering valve.
Figure 6:
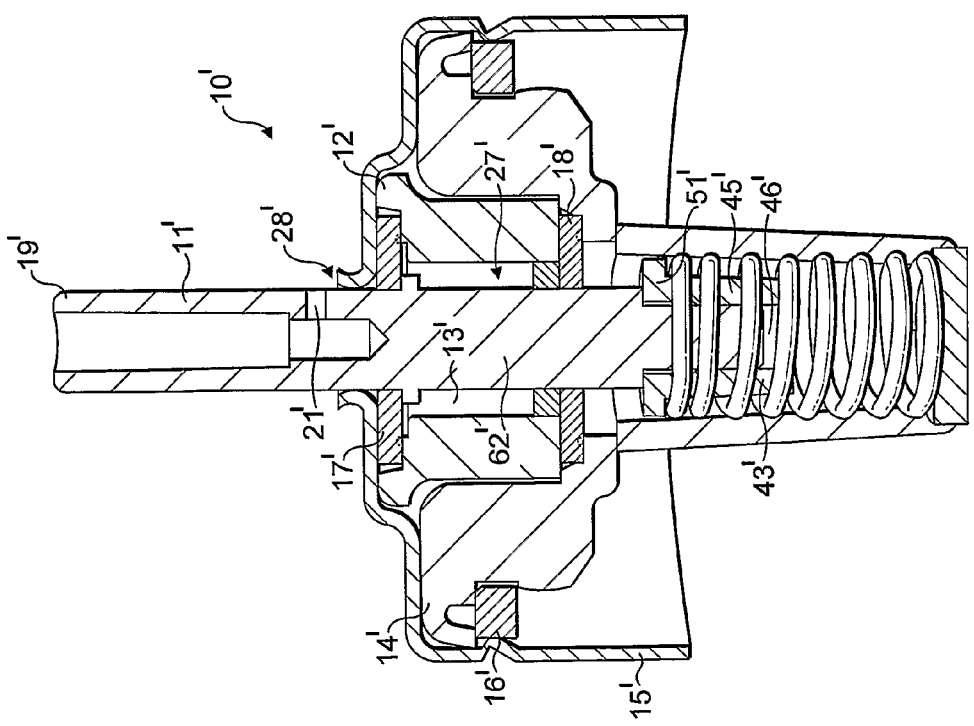
FIG. 6 is a partial cross-sectional view of the metering valve of FIG. 5 with certain internal components shown in perspective view.
Figure 7:
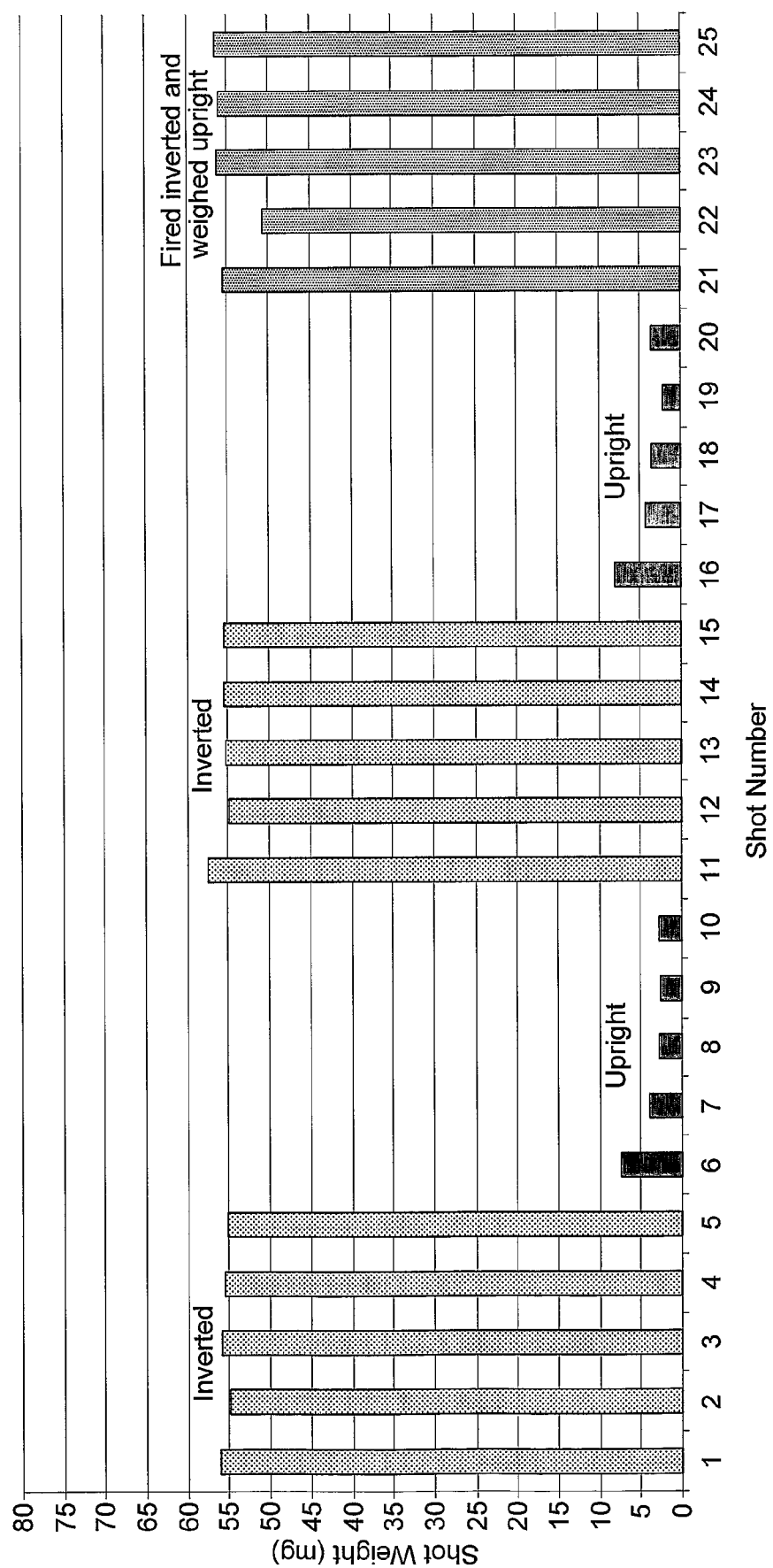
FIG. 7 is a graph showing shot weight versus shot number for the metering valve of FIG. 1 with the metering valve being actuated in both upright and inverted orientations.
Figure 8:
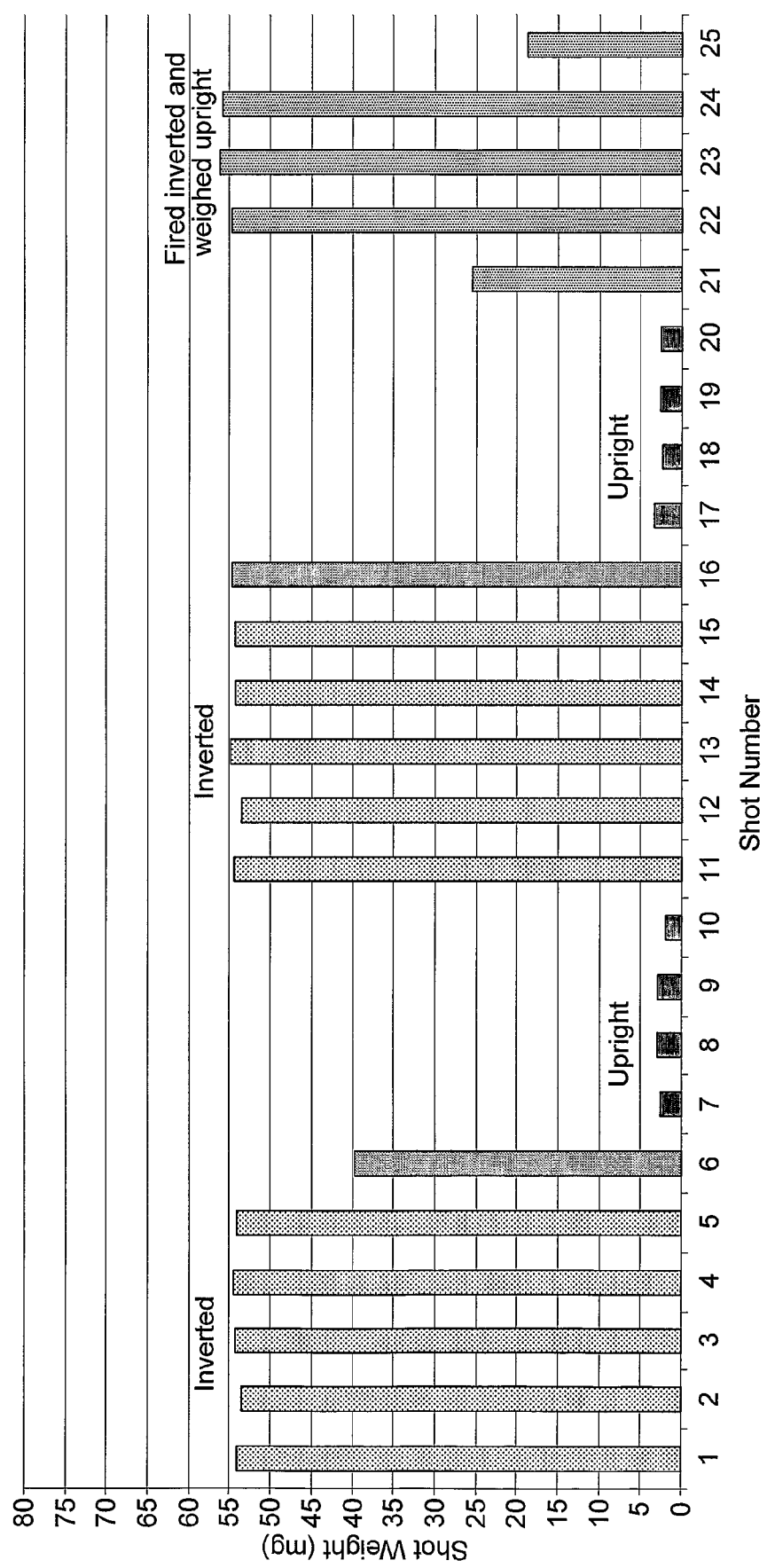
FIG. 8 is a graph showing shot weight versus shot number for the metering valve of FIG. 5 with the metering valve being actuated in both upright and inverted orientations.

FIG. 7 is a graph showing the results of the same testing regime applied to the valve of FIGS. 5 and 6 and described above. The graph shows shot weight in mg versus shot number for a metering valve 10 of the type shown in FIGS. 1 and 2 and described above with the metering valve being actuated in both upright and inverted orientations. The valve is actuated at a time interval of 10 seconds between actuations and was tested dispensing an inactive product containing a 134a HFA propellant with a 10% ethanol co-solvent. As can be seen, compared to the performance of the prior art valve of FIGS. 5 and 6 shown in the graph of FIG. 8, the valve 10 produces a very consistent dosage volume immediately on inversion. This indicates fast and consistent filling of the metering chamber 13 is taking place. In addition, the valve shows better drainage performance as indicated by the very low levels of discharge on the first actuation immediately after the valve is turned upright.

Figure 4:
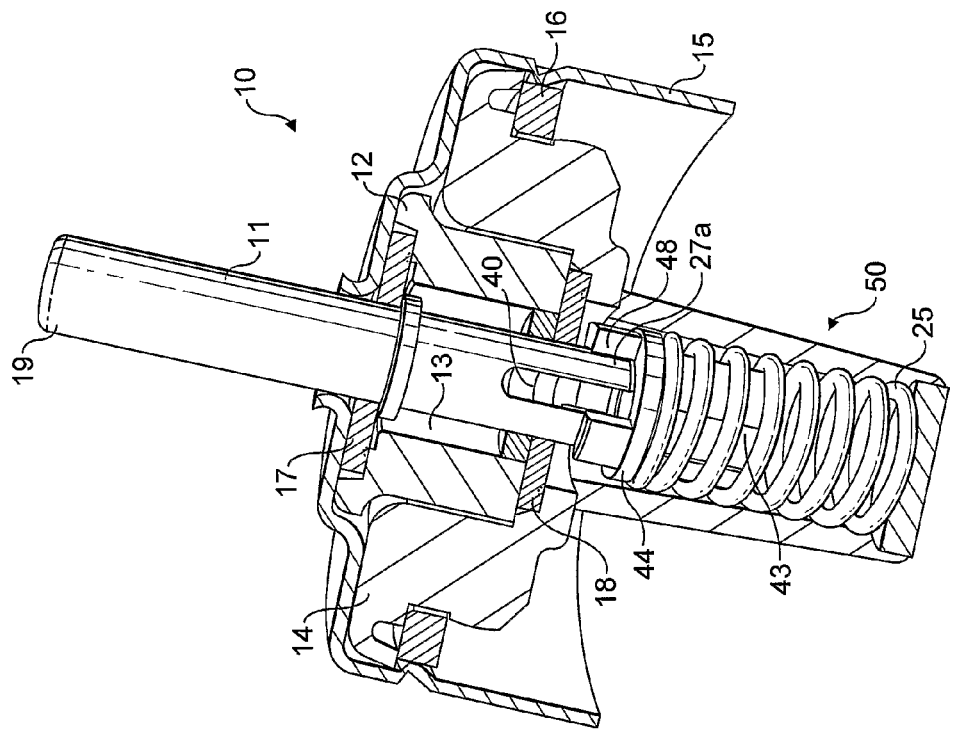
FIG. 4 is a partial cross-sectional view of the metering valve of FIG. 3 with certain internal components shown in perspective view.
Figure 3:
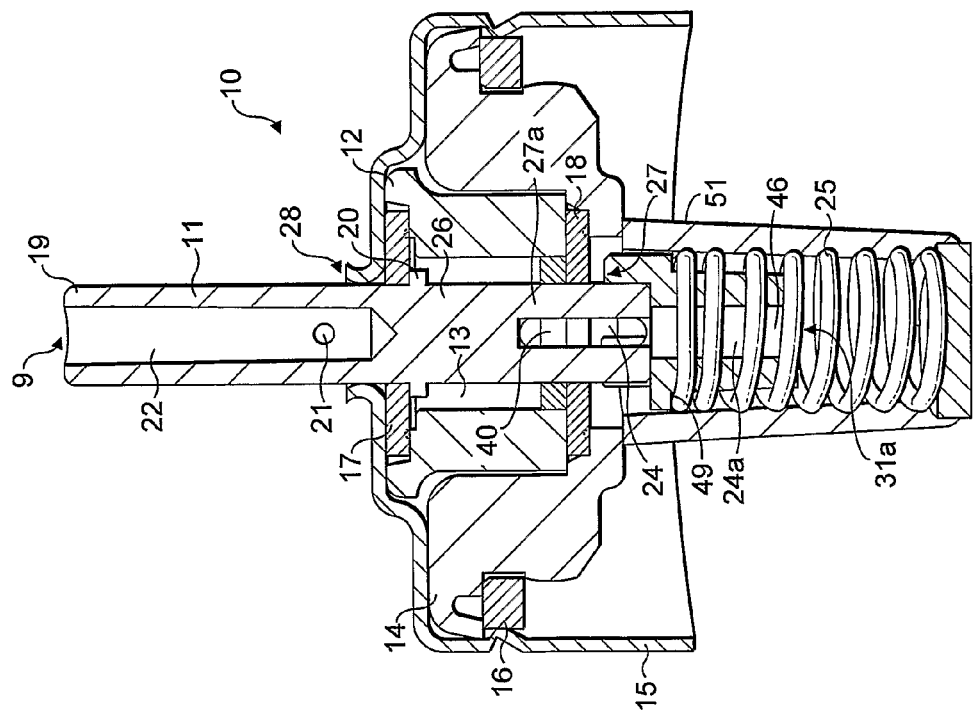
FIG. 3 is a cross-sectional view of a second embodiment of metering valve according to the present invention in a non-dispensing position.

FIGS. 3 and 4 illustrate a second embodiment of metering valve according to the present invention. Like components to those described above with reference to the first embodiment have been marked with like numerals and will not be described fully here. Instead, the differences between the first and second embodiments will be described.

In the second embodiment, the inner section 27 of the valve stem assembly 11 is truncated. The inner section comprises two dependent, C-shaped legs 27a which extend inwardly from the mid-section 26 of the valve stem assembly. The closed-ended slots 40 of the first embodiment are modified to comprise open-ended slots 40 which extend from the distal end of the inner section 27 towards the mid-section 26. As before a central passage 24 is formed between the legs 27a of the inner section 27. A stem cap 45 is again provided. However, in this embodiment, the inner section 27 does not extend into the central bore 46 of the stem cap 45 but abuts against an upper face of the flange 44. The projections 48 prevent lateral movement of the inner section 27 and the stem cap 45. The bore 46 of the stem cap 45 forms a continuation 24a of the central passage 24 of the inner section 27. A lower end 31a of the bore 46 acts as the inner end of the central passage 24.

Operation of the valve is the same as the first embodiment and the fluid flow on filling and draining of the metering chamber 13 is similar. Fluid enters the metering chamber via the central passage 24/24a and slots 40. As before it is believed that the jet of fluid flowing towards the inner seal 18 through the passages 24a and 24 acts to break up the liquid-vapour interface leading to better filling performance.

The construction of the valve stem assembly 11 of the second embodiment has the added advantage that the moulding of the components is more straightforward than those of the first embodiment. In particular the formation of the open-ended slots of the second embodiment is simpler than that of the closed-ended slots of the first embodiment.

The invention claimed is:

1. A metering valve for use with a pressurised dispensing container, the metering valve comprising a valve stem assembly co-axially slidable within an annular metering chamber defined between the valve stem assembly and a substantially cylindrical chamber body, the metering valve further comprising an outer seal extending between the valve stem assembly and the chamber body to seal off an outer duct of the valve stem assembly from the metering chamber when the valve stem assembly is in a non-dispensing position and an inner seal extending between the valve stem assembly and the chamber body, the valve stem assembly comprising a straight, central passage extending from an open inner end of the valve stem assembly to a mid-point of the valve stem assembly located longitudinally within the metering chamber, wherein the valve stem assembly further comprises at least two elongated openings in a wall of the valve stem assembly to allow radially-directed flow between an exterior of the valve stem assembly and the central passage, the elongated openings being located to extend either side of the inner seal when the valve stem assembly is in the non-dispensing position;

wherein the valve stem assembly comprises at least two parts which include a stem part or parts and a cap part with the cap part being slidingly received on the stem part or parts, and wherein the cap part comprises a bore and the stem part or parts comprises a tubular extension that is received within the bore when the cap part is assembled with the stem part or parts.

2. A metering valve as claimed in claim 1 wherein the at least two elongated openings comprise only two elongated openings in the valve stem assembly.

3. A metering valve as claimed in claim 2 wherein the two elongated openings are diametrically opposed to one another.

4. A metering valve as claimed in claim 1 wherein the elongated openings have a width of 0.50 mm to 2.00 mm.

5. A metering valve as claimed in claim 4 wherein the elongated openings have a width of 1.00 mm.

6. A metering valve as claimed in claim 1 wherein the elongated openings have a length of approximately 4.50 mm.

7. A metering valve as claimed in claim 1 wherein the elongated openings have a length of 4.20 mm.

8. A metering valve as claimed in claim 1 wherein the central passage is cylindrical.

9. A metering valve as claimed in claim 1 wherein the central passage has a constant internal diameter.

10. A metering valve as claimed in claim 9 wherein the central passage has an internal diameter which is substantially equal to a width of the elongated openings.

11. A metering valve as claimed in claim 1 wherein the central passage has an internal diameter of 0.50 mm to 2.00 mm.

12. A metering valve as claimed in claim 9 wherein the central passage has a width of 1.00 mm.

13. A metering valve as claimed in claim 1 wherein the elongated openings are orientated longitudinally in the valve stem assembly.

14. A metering valve as claimed in claim 1 wherein the elongated openings extend from a mid-point of the central passage to an upper end of the central passage.

15. A metering valve as claimed in claim 1 wherein the cap part comprises a plurality of upwardly directed projections which constrain lateral movement of the stem part or parts when the cap part is assembled with the stem part or parts.

16. A metering valve as claimed in claim 15 wherein the upwardly directed projections extend upwardly into proximity with an undersurface of the inner seal such that on movement of the valve stem assembly into the non-dispensing position the projections are enabled to contact and displace the inner seal in the event that the inner seal is displaced inwards by the valve stem assembly.

17. A metering valve as claimed in claim 1 wherein the stem part or parts define the central passage.

18. A metering valve as claimed in claim 1 wherein the elongated openings are in the form of slots extending from an upper end of the tubular extension towards the mid-point of the valve stem assembly.

19. A metering valve as claimed in claim 1 wherein the cap part comprises a bore and the cap part and stem part or parts together define the central passage.

20. A metering valve as claimed in claim 19 wherein the stem part or parts does not substantially extend within the bore of the cap part.

21. A metering valve as claimed in claim 19 wherein the elongated openings are in the form of open-ended slots extending from a distal end of the stem part or parts towards the mid-point of the valve stem assembly.

22. A metering valve as claimed in claim 21 wherein the stem part or parts comprises two dependent legs formed between the open-ended slots.

23. A metering valve as claimed in claim 1 wherein one or more components of the metering valve have a layer of one or more polymerised monomers bonded to at least a portion thereof.

24. A metering valve as claimed in claim 23 wherein the one or more monomers are selected from the group of materials comprising perfluoro-cyclohexane, perfluoro-hexane, tetrafluoroethylene, trifluoroethylene, vinylidene fluoride, vinylfluoride, fluoroethylene, fluoropropylene, a siloxane, a silazane, and a parylene.

25. A metering valve as claimed in claim 1 wherein any of the inner seal, outer seal and gaskets of the valve are formed from any of nitrile, EPDM and other thermoplastic elastomers, butyl or neoprene.

26. A metering valve as claimed in claim 1 wherein any of the rigid components of the valve, such as the valve body, chamber body and valve stem assembly are formed from polyester, nylon, acetal, stainless steel, ceramics or glass.

27. A metering valve for use with a pressurised dispensing container, the metering valve comprising:
a valve stem assembly co-axially slidable within an annular metering chamber defined between the valve stem assembly and a substantially cylindrical chamber body;
an outer seal extending between the valve stem assembly and the chamber body to seal off an outer duct of the valve stem assembly from the metering chamber when the valve stem assembly is in a non-dispensing position;
an inner seal extending between the valve stem assembly and the chamber body, and
the valve stem assembly comprising a hollow central bore defining a straight central passage that extends from an open inner end of the valve stem assembly to a mid-point of the valve stem assembly located longitudinally within the metering chamber, and
wherein the valve stem assembly further comprises at least two elongated openings in a wall of the valve stem assembly to allow radially-directed flow between an exterior of the valve stem assembly and the central passage, the elongated openings extending to opposite sides of the inner seal when the valve stem assembly is in the non-dispensing position;
wherein the valve stem assembly comprises a stem part and a cap part, with said cap part and stem part each having a central bore section with the central bore sections forming together the hollow central bore defining the straight central passage.

28. A metering valve as claimed in claim 27 wherein the cap part comprises a plurality of upwardly directed projections which constrain lateral movement of the stem part when the cap part is assembled with the stem part, and which upwardly directed projections are spaced apart as to enable radial fluid flow into and out of the elongated openings.

29. A metering valve for use with a pressurised dispensing container, the metering valve comprising a valve stem assembly co-axially slidable within an annular metering chamber defined between the valve stem assembly and a substantially cylindrical chamber body, the metering valve further comprising an outer seal extending between the valve stem assembly and the chamber body to seal off an outer duct of the valve stem assembly from the metering chamber when the valve stem assembly is in a non-dispensing position and an inner seal extending between the valve stem assembly and the chamber body, the valve stem assembly comprising a straight, central passage extending from an open inner end of the valve stem assembly to a mid-point of the valve stem assembly located longitudinally within the metering chamber, wherein the valve stem assembly further comprises at least two elongated openings in a wall of the valve stem assembly to allow radially-directed flow between an exterior of the valve stem assembly and the central passage, the elongated openings being located to extend either side of the inner seal when the valve stem assembly is in the non-dispensing position;
wherein the valve stem assembly comprises at least two parts which include a stem part or parts and a cap part; and
wherein the cap part comprises a bore and the cap part and stem part or parts together define the central passage.

30. A metering valve as claimed in claim 29 wherein the stem part or parts does not substantially extend within the bore of the cap part.

31. A metering valve as claimed in claim 29 wherein the elongated openings are in the form of open-ended slots extending from a distal end of the stem part or parts towards the mid-point of the valve stem assembly.

32. A metering valve as claimed in claim 31 wherein the stem part or parts comprises two dependent legs formed between the open-ended slots.

33. A metering valve as claimed in claim 27 wherein the cap part comprises a plurality of upwardly directed projections which constrain lateral movement of the stem part when the cap part is assembled with the stem part,
wherein the upwardly directed projections extend upwardly into proximity with an undersurface of the inner seal such that on movement of the valve stem assembly into the non-dispensing position the projections are enabled to contact and displace the inner seal in the event that the inner seal is displaced inwards by the valve stem assembly.

* * * * *